US012616551B2

(12) United States Patent
Sykes et al.

(10) Patent No.: US 12,616,551 B2
(45) Date of Patent: May 5, 2026

(54) MECHANISM FOR RETAINING A MARKER

(71) Applicant: Merit Medical Systems, Inc., South Jordan, UT (US)

(72) Inventors: Kenneth Sykes, Bluffdale, UT (US); Steven Weir, Sandy, UT (US); Emilio Aguilar, South Jordan, UT (US); Richard P. Jenkins, Bluffdale, UT (US); Jim Mottola, West Jordan, UT (US); Michael Dean Haslam, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 48 days.

(21) Appl. No.: 18/350,324

(22) Filed: Jul. 11, 2023

(65) Prior Publication Data

US 2024/0016573 A1 Jan. 18, 2024

Related U.S. Application Data

(60) Provisional application No. 63/368,186, filed on Jul. 12, 2022.

(51) Int. Cl.
| | |
|---|---|
| *A61B 90/00* | (2016.01) |
| *A61B 17/34* | (2006.01) |
| *A61M 37/00* | (2006.01) |

(52) U.S. Cl.
CPC .......... *A61B 90/39* (2016.02); *A61B 17/3468* (2013.01); *A61M 37/0069* (2013.01); *A61B 2090/3987* (2016.02)

(58) Field of Classification Search
CPC ............ A61B 90/39; A61B 2090/3987; A61B 17/3468; A61B 17/3417; A61B 2017/12054; A61B 2017/1205; A61B 2017/00623; A61B 2017/22035; A61B 2560/063; A61M 37/0069; A61M 2005/1585; A61M 5/3286;

(Continued)

(56) References Cited

U.S. PATENT DOCUMENTS

| | | | |
|---|---|---|---|
| 6,471,700 B1 | 10/2002 | Burbank et al. | |
| 7,247,160 B2 | 7/2007 | Seiler et al. | |

(Continued)

FOREIGN PATENT DOCUMENTS

| | | | | |
|---|---|---|---|---|
| WO | WO-2016073912 A1 * | 5/2016 | ............. | A61B 10/02 |
| WO | WO-2017019631 A1 * | 2/2017 | ............ | A61M 5/425 |

OTHER PUBLICATIONS

International Search Report and Written Opinion dated Oct. 25, 2023 for PCT/US2023/069959.

(Continued)

*Primary Examiner* — Keith M Raymond
*Assistant Examiner* — Johnathan Maynard
(74) *Attorney, Agent, or Firm* — Dorsey & Whitney LLP

(57) ABSTRACT

A device, and methods for using said device, for inserting a marker into a patient's body. The device may comprise a retention mechanism to hold the device in an first, undeployed, state. The device may be inserted into a patient's body in the first state, transitioned by the user into a second state wherein the retention mechanism is overcome, and then transition the device into a third state to deliver a marker to a precise location. The device may then be removed from the patient's body.

15 Claims, 6 Drawing Sheets

(58) Field of Classification Search
CPC .......... A61M 2005/2073; A61M 25/01; A61M
5/3134; A61M 5/31571; A61N 1/375;
A61N 2005/1009; A61N 2005/1011;
A61F 13/266; A61F 2/95; A61F 2/9522;
A61F 2/966; A61F 2002/9665
See application file for complete search history.

(56) References Cited

U.S. PATENT DOCUMENTS

| | | | |
|---|---|---|---|
| 2003/0233101 A1* | 12/2003 | Lubock | A61B 90/39 |
| | | | 606/116 |
| 2004/0019126 A1 | 1/2004 | Brand et al. | |
| 2004/0127765 A1 | 7/2004 | Seiler et al. | |
| 2007/0142725 A1 | 6/2007 | Hardin et al. | |
| 2008/0294039 A1 | 11/2008 | Jones et al. | |
| 2010/0160777 A1 | 6/2010 | Hardin et al. | |
| 2014/0276037 A1 | 9/2014 | Johnson et al. | |
| 2016/0045475 A1* | 2/2016 | Day | A61K 45/06 |
| | | | 514/156 |
| 2016/0128784 A1* | 5/2016 | Ahari | A61B 10/02 |
| | | | 600/432 |
| 2017/0100162 A1* | 4/2017 | Campbell | A61B 90/03 |
| 2017/0105739 A1* | 4/2017 | Dias | A61B 90/39 |
| 2017/0231716 A1* | 8/2017 | Ahari | A61B 10/02 |
| | | | 600/431 |
| 2019/0117259 A1* | 4/2019 | Forsberg | A61B 17/34 |
| 2019/0321014 A1 | 10/2019 | Coonahan et al. | |
| 2024/0307697 A1* | 9/2024 | Mullins | A61N 1/0551 |

OTHER PUBLICATIONS

European Search Report dated Mar. 13, 2026 issued in European patent application No. 23840462.8.

* cited by examiner

MECHANISM FOR RETAINING A MARKER

RELATED CASES

This application claims priority to U.S. Provisional Application No. 63/368,186, filed on Jul. 12, 2022 and titled "MECHANISM FOR RETAINING A MARKER," which is hereby incorporated by reference in its entirety.

TECHNICAL FIELD

The present disclosure relates generally to devices and methods for retaining a marker with a delivery system, for example in the field of tumor or cancer localization. More particularly, some embodiments relate to lumpectomy, and localization in preparation for lesion removal.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
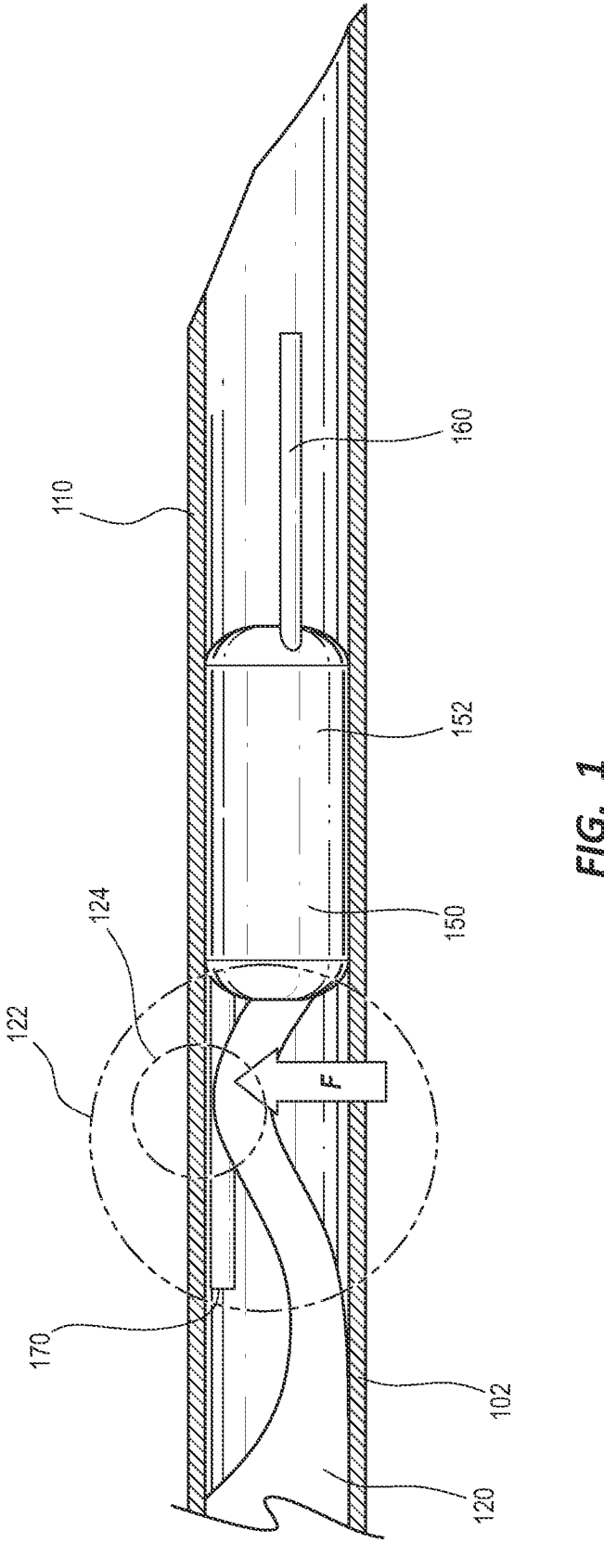
FIG. 1 is a first exemplary embodiment of a marker retention device.

Before a biopsy or surgical procedure to remove a lesion within a breast, such as a lumpectomy procedure, the location of the lesion must be identified. For example, mammography or ultrasound imaging may be used to identify and/or confirm the location of the lesion before a procedure. The resulting images may be used by a surgeon during a subsequent procedure to identify the location of the lesion and guide the surgeon, e.g., during dissection to access and/or remove the lesion. Such images may be two dimensional, and therefore provide limited guidance for localization of the lesion.

To facilitate localization in three dimensions, a marker may be placed with an insertion device to provide localization information during a procedure. For example, an insertion device for a marker may be introduced through a breast into a lesion, and in conjunction with mammography or any other standard imaging technique, a marker may be deployed from the insertion device into the lesion. The insertion device may then be withdrawn, and the position of the marker may be confirmed using mammography. During a subsequent surgical procedure, a hand-held probe may be placed over the breast to identify a location overlying the marker. An incision may be made and the probe may be used to guide excision of the marker and lesion.

Markers and placement devices within the scope of this disclosure may be used for locating lesions and placing markers at any location within the body. Specific examples given herein, such as placement of a marker within breast tissue to identify a breast cancer lesion, may be analogized to placement within other areas of the body.

A known problem with conventional insertion devices is that the insertion device, through a variety of factors, may be prematurely and/or accidently actuated, resulting in premature or partial delivery including possible loss of precision in placement of the marker. For example, the device may be accidentally actuated during packaging, transportation, or preparation for use, resulting in partial or complete premature deployment. Accidental actuation may further be due to a variety of factors, including but not limited to: the design of the actuation mechanism and its handling during packaging, delivery, and pre-operation preparation, the robustness and durability of the actuation mechanism, ease of use provided to the user in deploying the marker, or any combination of these and other additional factors.

Accordingly, there is a need for apparatus and methods for accurately and intuitively placing a marker or other tissue structures in advance of and/or during surgical, diagnostic, while maintaining the integrity and security of the deployment mechanism prior to its usage. In some embodiments, devices within the scope of this disclosure may be broadly directed to such a system and methods for inserting structures, including a marker, into the body of a patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical, fluidic and thermal interaction. Thus, two components may be coupled to each other even though they are not in direct contact with each other. The phrases "attached to" or "attached directly to" refer to interaction between two or more entities which are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Turning to the drawings, FIG. 1 shows an exemplary embodiment of a system 100 for retaining a marker within an inserter device. System 100 may include inserter device 102 and marker 150. Inserter device 102 may include cannula 110 and stylet 120. Stylet 120 may included biased portion 122 and engaging portion 124. Marker 150 may include body portion 152, distal antenna 160, and proximal antenna 170.

Biased portion 122 of stylet may comprise a bend or other deformity that engages with an antenna of the marker 150. In this embodiment, biased portion 122 comprises engaging portion 124, that may be a bend, to engage with marker 150.

In this embodiment, engaging portion 124 of stylet 120 may exert a force on proximal antenna 170 of marker 150. This force may enhance and/or provide frictional force between antenna 170 and the inner wall of cannula 110. This force may be exerted from engaging portion 124 in the outward radial direction. This force may retain or aid in retaining marker 150 within the cannula 110 until the user is ready to deploy the marker.

A person of ordinary skill in the art, having the benefit of this disclosure, may be able to envision multiple geometries and/or configurations for the stylet 120 to exert a force on the antenna 170 of marker 150.

Figures 2A, 2B:
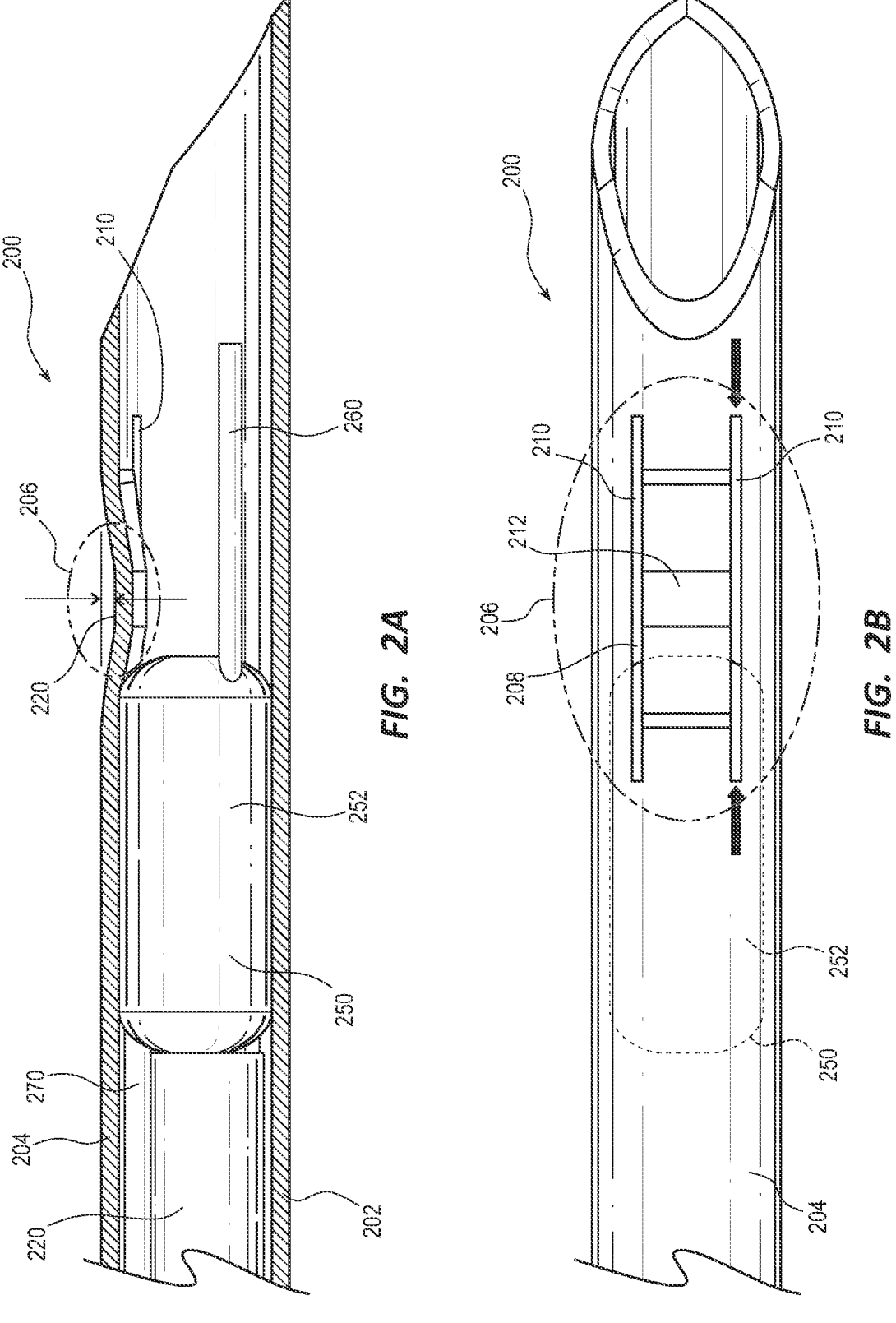
FIG. 2A is a side view of a second exemplary embodiment of a marker retention device.
FIG. 2B is a top view of the second exemplary embodiment of a marker retention device.

In an additional exemplary embodiment, FIGS. 2A and 2B depict a system 200 for retaining a marker within an inserter device. System 200 may include and inserter device 202 and a marker 250. Inserter device 202 may include cannula 204 and stylet 220. Cannula 204 may comprise an indented bridge 206. Indented bridge 206 may further comprise a first slit 208, a second slit 210, and a lowered portion 212. Marker 250 may comprise body portion 252, distal antenna 260, and proximal antenna 270.

In this embodiment, indented bridge 206 may provide a constriction, or obstacle, in the inner wall of the cannula 204. This constriction may provide a force that may be frictional to prevent marker 250 from prematurely deploying. A user may overcome this force when the marker is desired to be deployed.

Indented bridge 206 may be bent radially inwards a distance of 0.003 to 0.005 inches; although a person of ordinary skill in the art, having the benefit of this disclosure, will be able to envision various configurations and/or dimensions for indented bridge 206 to provide a force against the premature deployment of marker 250.

Figures 3, 4:
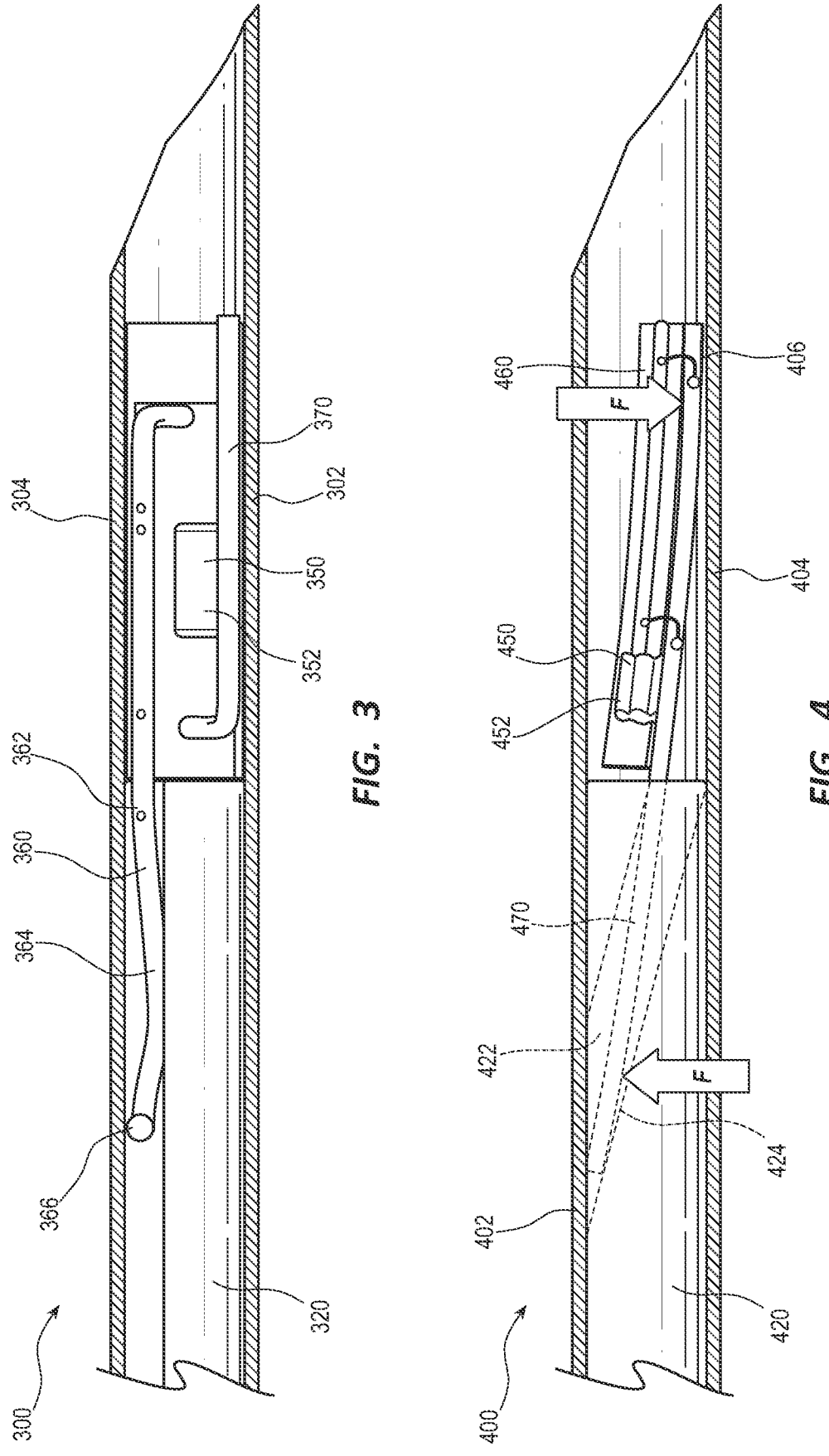
FIG. 3 is a third exemplary embodiment of a marker retention device.
FIG. 4 is a fourth exemplary embodiment of a marker retention device.

FIG. 3 depicts an additional exemplary embodiment of a system 300 for retaining a marker within an inserter device. System 300 may include an inserter device 302 and a marker 350. Inserter device 302 may comprise cannula 304 and stylet 320. Marker 350 may include body portion 352, proximal antenna 360, and distal antenna 370. Proximal antenna 360 may comprise pre-bend portion 362, bend 364, and post-bend portion 366.

In this embodiment, stylet 320 may comprise a slot that allows proximal antenna 360 to extend in the proximal direction.

Proximal antenna 360, including pre-bend portion 362, bend 364, and post-bend portion 366, may serve to provide an outward radial force on the inner wall of cannula 304. This force may serve to provide a frictional force that aids in retaining the marker 350 within the cannula prior to deployment. Upon deployment, the user may overcome this force to deploy the marker 350.

Post-bend portion 366 may provide the contact point with the cannula 304 to deliver force to the inner wall of cannula 304. However, a person of ordinary skill in the art, having the benefit of this disclosure, would be able to envision various configurations and/or dimensions for proximal antenna 360 to provide a force against the premature deployment of marker 350.

FIG. 4 depicts an exemplary embodiment of a system 400 for retaining a marker within an inserter device. System 400 may include inserter device 402 and marker 450. Inserter device 402 may include cannula 404 and stylet 420. Cannula 404 may include first contact point 406. Stylet 420 may include channel 422, and second contact point 424. Marker 450 may include body portion 452, distal antenna 460, and proximal antenna 470.

As seen in FIG. 4, channel 422 in stylet 420 may be angled so as to provide a force and a bend on proximal antenna 470 when it is inside the channel. This force on proximal antenna 470 may create a related force on a distal portion of the marker body portion 452. Both of these forces at both of these points may create and/or increase a frictional force that may function to retain marker 450 within the cannula 404 until the user decides to overcome the force and deploy the marker 450.

A person of ordinary skill in the art, having the benefit of this disclosure, would be able to envision various angles, placements, and/or dimensions for channel 422 so as to provide a sufficient interaction with proximal antenna 470, and commensurate retaining force on marker 450.

Figures 5, 6:
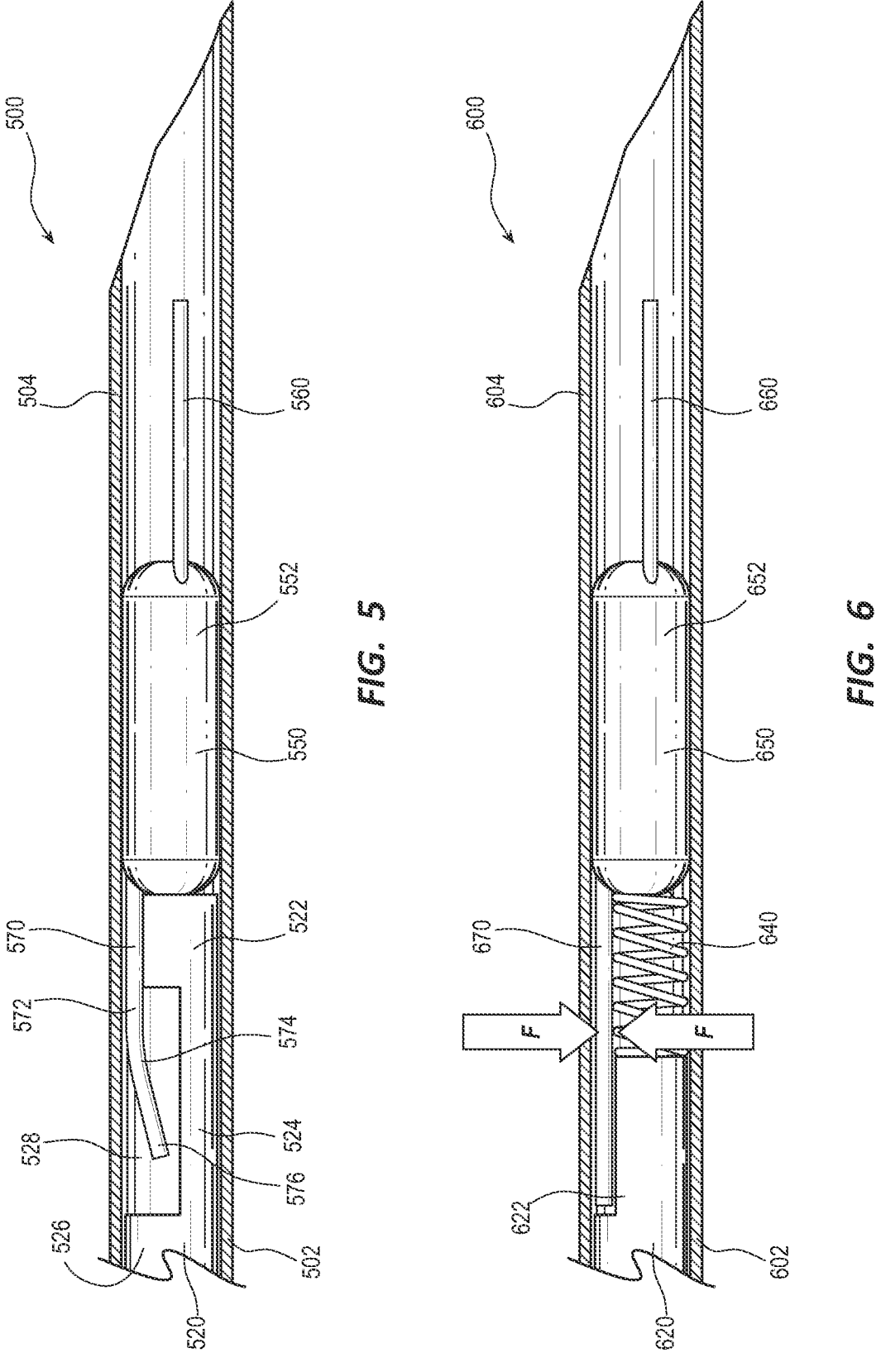
FIG. 5 is a fifth exemplary embodiment of a marker retention device.
FIG. 6 a sixth exemplary embodiment of a marker retention device.

FIG. 5 illustrates an exemplary embodiment of a system 500 for retaining a marker within an inserter device. System 500 may include inserter device 502 and marker 550. Inserter device 502 may include cannula 504 and stylet 520. Stylet 520 may further include distal portion 522, thin portion 524, main body portion 526, and gap 528. Marker 550 may include body portion 552, distal antenna 560, and proximal antenna 570. Proximal antenna 570 may include pre-bend portion 572, bend 574, and post-bend portion 576.

Proximal antenna 570 may interact with stylet 520 in that bend 574 and post-bend portion 576 of the antenna 570 may reside in gap 528 of stylet 520. The radial distance between distal portion 522 of stylet 520, and the inner wall of cannula 504, may be great enough to contain proximal antenna 570 with negligible friction, but the distance may not be so large that bend 574 and post-bend portion 576 may pass through. Bend 574 and post-bend portion 576 may rest in gap 528 of stylet 520. Thus, the marker may be held in place, until a user decides to actuate the inserter device, and deploy marker 550.

A person of ordinary skill in the art, having the benefit of this disclosure, would be able to envision various dimensions for gap 528, and angles of bend 574, including various placements, and/or configurations for the stylet and antenna, that are configured to hold the marker 550 within the cannula 504 prior to deployment.

FIG. 6 depicts an exemplary embodiment of a system 600 for retaining a marker within an inserter device. System 600 may comprise inserter device 602, spring 640, and marker 650. Inserter device 602 may further comprise cannula 604 and stylet 620. Stylet 620 may comprise gap portion 622. Marker 650 may comprise body portion 652, distal antenna 660, and proximal antenna 670.

Spring 640 may provide a radial outward force on proximal antenna 670. Proximal antenna 670 may be forced into contact with the inner wall of cannula 604 through the radial outward force. This may provide a frictional force against movement of the marker 650 within the cannula that may be overcome once the user has decided to deploy marker 650.

Spring 640 may be held in place by being wrapped around the gap portion 622 of stylet 620. However, a person of ordinary skill in the art, having the benefit of this disclosure, would be able to envision various mechanisms and configurations to hold the spring in place.

5

Figures 7, 8A, 8B:
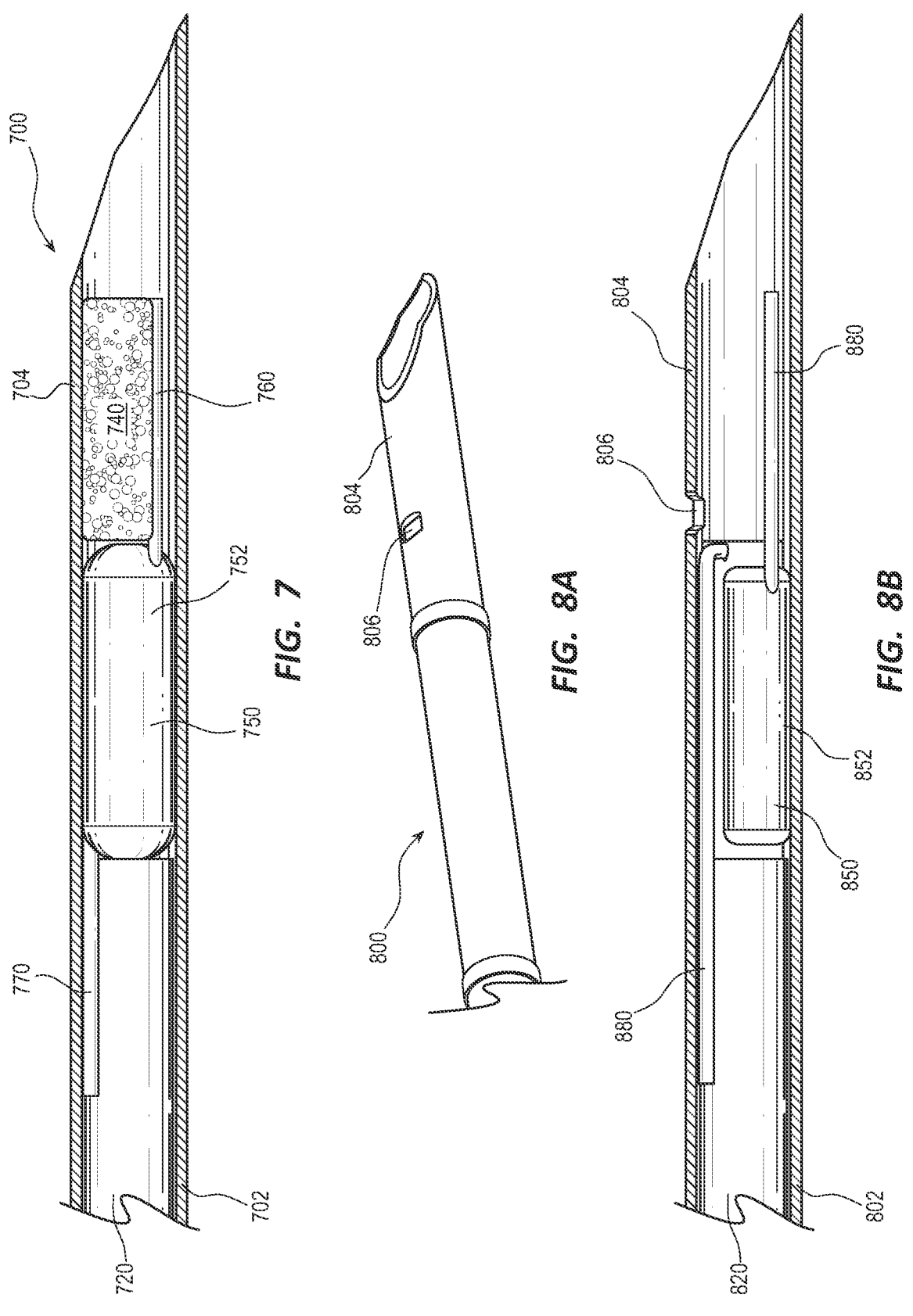
FIG. 7 is a seventh exemplary embodiment of a marker retention device.
FIG. 8A is a perspective view of an eighth exemplary embodiment of a trigger of the marker inserter device.
FIG. 8B is a cutaway view of the eighth exemplary embodiment of a trigger of the marker inserter device.

FIG. 7 illustrates an exemplary embodiment of a system 700 for retaining a marker within an inserter device. System 700 may comprise inserter device 702, plug 740, and marker 750. Inserter device 702 may comprise cannula 704 and stylet 720. Marker 750 may comprise body portion 752, distal antenna 760, and proximal antenna 770.

Plug 740 may be biodegradable and provide a frictional force against movement of the marker prior to deployment.

FIGS. 8A and 8B illustrate an exemplary embodiment of a system 800 for retaining a marker within an inserter device. System 800 may comprise inserter device 802 and marker 850. Inserter device 802 may comprise cannula 804, and stylet 820. Cannula 804 may comprise deformation portion 806. Marker 850 may comprise body portion 852, distal antenna 860, and proximal antenna 870.

Deformation portion 806 may be a dimple or deformed portion in the cannula protruding radially inward. Deformation portion 806 may further constrict the movement of marker 850 within the cannula 804. A user may operate the device by pushing marker 850 in the distal direction, past deformation portion 806, when deployment is desired.

Figure 9:
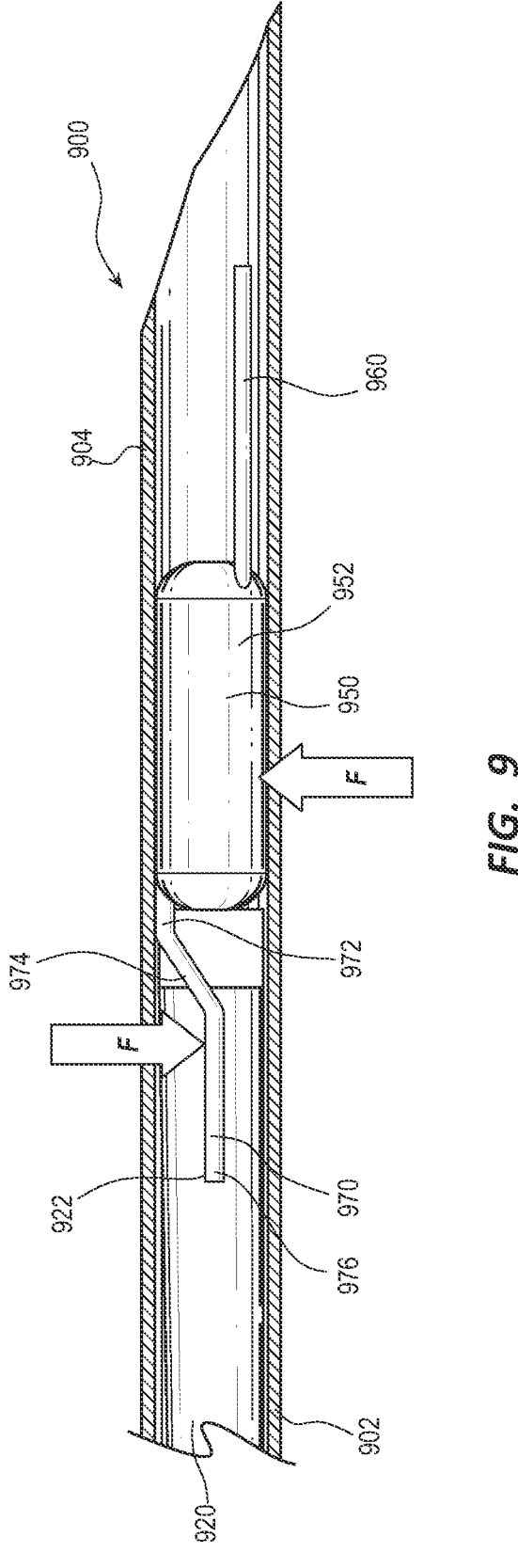
FIG. 9 is a ninth exemplary embodiment of a stylet of the marker inserter device.

FIG. 9 illustrates a further exemplary embodiment of a system 900 for retaining a marker within an inserter device. System 900 may comprise inserter device 92 and marker 950. Inserter Device 902 may comprise cannula 904 and stylet 920. Stylet 920 may comprise slot 922. Marker 950 may comprise body portion 952, distal antenna 960, and proximal antenna 970. Proximal antenna 970 may comprise pre-bend portion 972, bend 974, and post-bend portion 976.

Slot 922 may be concentrically center in stylet 920. Post-bend portion 976 of proximal antenna 970 may rest in slot 922. Bend 974 in antenna may serve such that stylet 920 provides an inward radial force on proximal antenna 970. This inward radial force may provoke a commensurate radial force on body portion 952, exerted by the inner wall of cannula 904. This force may aid in increasing a frictional force between the inner wall of cannula 904 and body portion 952, so as to oppose movement of the marker 950 within the cannula. Upon deployment, a user may overcome this frictional force to eject marker 950 from within cannula 904.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A system for implanting a marker in a patient's body, comprising:

a cannula;

a marker within the cannula;

a stylet configured to eject the marker from the cannula; and an indented bridge defined by the cannula configured to engage with and retain the marker within the cannula, wherein the indented bridge is disposed between two slots in the cannula and a portion of the indented bridge is bent radially inward, and wherein a distal portion and a proximal portion of the indented bridge are secured to the cannula.

2. The system of claim 1, wherein the marker comprises a proximal antenna and a distal antenna.

3. The system of claim 1, wherein the indented bridge of the cannula constricts an inner diameter of the cannula.

4. The system of claim 1, wherein the indented bridge is bent radially inwards a distance of 0.003 to 0.005 inches.

5. The system of claim 1, wherein the indented bridge comprises a flat lowered portion between the distal portion and the proximal portion of the indented bridge.

6. The system of claim 1, wherein the cannula further comprises a deformity that comprises a point deformation on an cannula inner wall.

7. The system of claim 1, wherein the stylet comprises a deformity.

8. The system of claim 7, wherein the deformity comprises a bend in the stylet configured to engage with an antenna of the marker.

9. The system of claim 7, wherein the deformity comprises a channel in the stylet.

10. The system of claim 9, wherein the channel is configured to receive an antenna of the marker.

11. The system of claim 9, wherein the channel is configured to provide a force on an antenna of the marker.

12. The system of claim 7, wherein the deformity comprises a cavity in the stylet.

13. The system of claim 12, wherein the cavity is configured to receive an antenna of the marker.

14. The system of claim 13, wherein the antenna comprises a bend.

15. The system of claim 1, wherein the marker comprises a deformity.

* * * * *